United States Patent [19]

Bonnyman et al.

[11] Patent Number: 4,851,515
[45] Date of Patent: Jul. 25, 1989

[54] PREPARATION OF $^{99m}$TC RADIOPHARMACEUTICALS

[75] Inventors: John Bonnyman, Nunawading; John Baldas, Rosanna East, both of Australia

[73] Assignee: The Commonwealth of Australia, Phillip, Australia

[21] Appl. No.: 774,592

[22] PCT Filed: Dec. 21, 1984

[86] PCT No.: PCT/AU84/00268
§ 371 Date: Aug. 23, 1985
§ 102(e) Date: Aug. 23, 1985

[87] PCT Pub. No.: WO85/03063
PCT Pub. Date: Jul. 18, 1985

[30] Foreign Application Priority Data

Dec. 29, 1983 [AU] Australia .................. PG3034/83

[51] Int. Cl.$^4$ ...................... A61K 49/02; C07F 13/00
[52] U.S. Cl. ........................ 534/14; 424/11; 423/2; 423/49
[58] Field of Search .............. 424/1.1; 436/548; 534/14, 10; 423/2

[56] References Cited

U.S. PATENT DOCUMENTS 4,208,398 6/1980 Kubiatowicz et al. .............. 424/1.1
4,323,546 4/1982 Crockford et al. .................. 424/1.1
4,421,735 12/1983 Haber et al. ........................ 424/1.1

FOREIGN PATENT DOCUMENTS 2101118 1/1983 United Kingdom ............... 424/1.1

OTHER PUBLICATIONS

Radioimmunogimaging and Radioimmunotherapy, S. W. Burchiel and B. A. Rhodes, Eds., Elsevier, New York 1983, pp. 207–222.
"Synthetic and Structural Aspects of Technetium Chemistry as Related to Nuclear Medicine":, Inorganic Chemistry in Biology and Medicine, Tc Chemistry, E. Duetsch and B. L. Barnet 1980, pp. 103–119.
Baldos et al., CA 96:57736f (1982).
Baldas et al. CA 97:60987q (1982).
Karde/ et al., CA 95:17322r (1981).
Baldas et al., CA 95:54003h (1981).
Baldas et al., CA 95:214309t (1981).

Primary Examiner—John F. Terapane
Assistant Examiner—J. E. Thomas
Attorney, Agent, or Firm—Cushman, Darby & Cushman

[57] ABSTRACT

Compounds of the formula I:

$$R + [^{99m}TcNX_4] - \quad \text{I}$$

wherein R+ represents a cation and X represents a halo group, are prepared by reaction with an azide compound in the presence of a hydrohalic acid. The compounds are useful in production of $^{99m}$Tc-labelled radiopharmaceuticals by reaction with ligands and monoclonal antibodies or antibody fractions.

4 Claims, 4 Drawing Sheets

F I G. 1
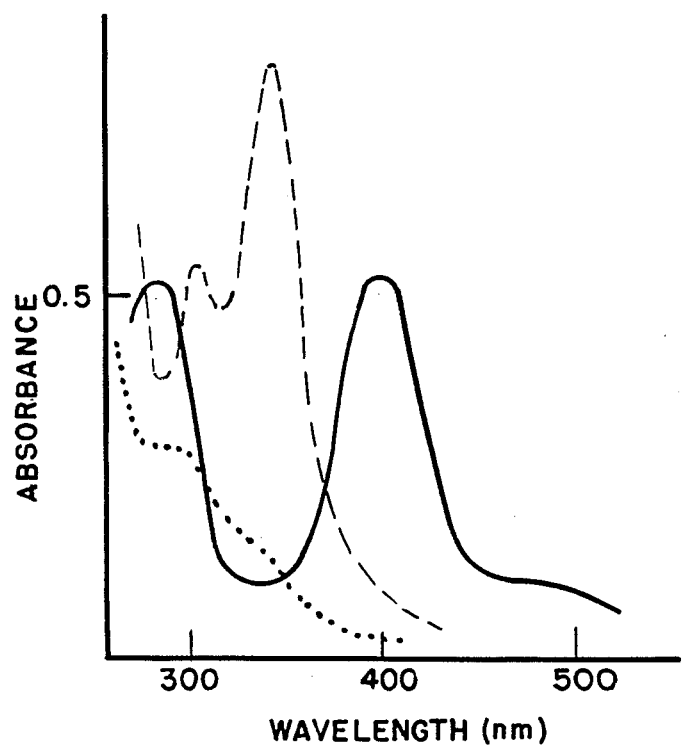

F I G. 2
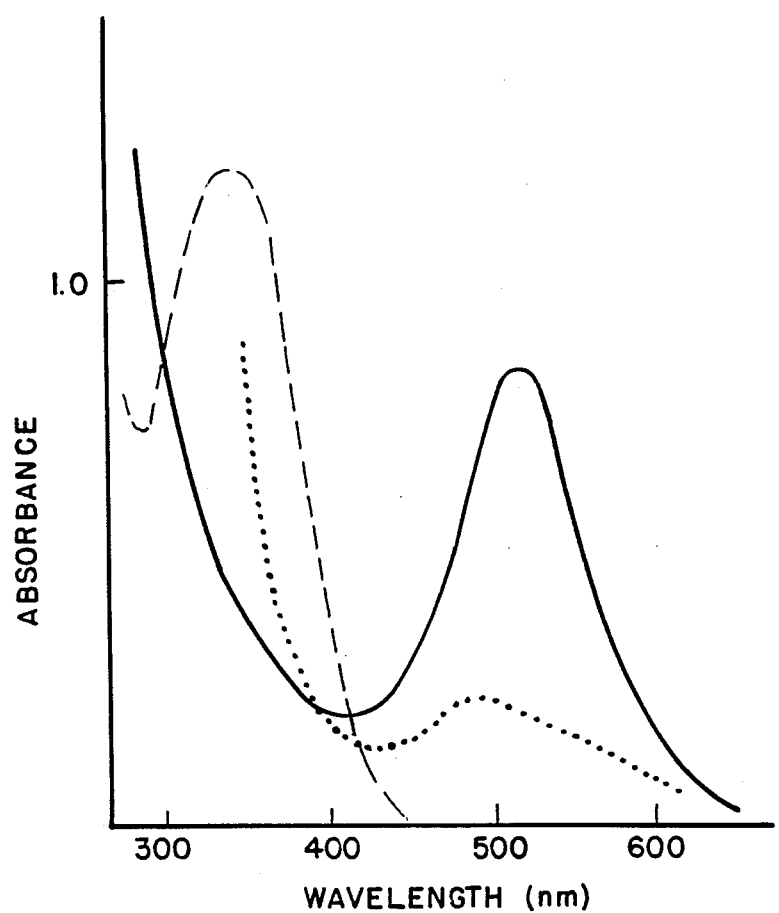

PREPARATION OF $^{99m}$TC RADIOPHARMACEUTICALS

This invention relates to the preparation of radiopharmaceuticals, and in particular to the preparation of technetium-99m ($^{99m}$Tc)—labelled radiopharmaceuticals.

Radiopharmaceuticals are diagnostic or therapeutic agents by virtue of the physical properties of their constituent radionuclides. Thus, their utility is not based on any pharmacologic action. Most clinically used drugs of this class are diagnostic agents incorporating a gamma-emitting nuclide which, because of its physical or metabolic properties, localizes in a specific organ after intravenous injection. Images reflecting organ structure or function are then obtained by means of a scintillation camera that detects the distribution of ionizing radiation emitted by the radioactive drug. The principal isotope currently used in clinical diagnostic nuclear medicine is reactor-produced metastable technetium-99m.

Many methods have been described for the reduction of pertechnetate ($^{99m}Tc^{VII}O_4^-$) in the preparation of $^{99m}$Tc-radiopharmaceuticals. Reducing agents which have been used include stannous ion, electrolysis, ferrous ion, ferrous-ascorbate, formamidine sulphinic acid and sodium borohydride (Deutsch et a., 1983). These labelling procedures generally lead to the reduction of technetium to the Tc(IV) or Tc(V) oxidation state. In many cases the compound prepared contains the TcO moiety (Deutsch, 1979). Because of problems experienced with these reducing agents, the use of a substitution route for the production of $^{99m}$Tc-radipharmaceuticals has been advocated (Deutsch & Barnett, 1980). The agents normally used for substitution reactions are $TcOX_5^{2-}$ and $TcX_6^{6-}$ (X=Cl, Br) in which technetium is in the $Tc^V$ and $Tc^{IV}$ valency states respectively.

The present inventors have investigated the preparation of $^{99m}$Tc-radiopharmaceuticals containing the TcN moiety, and have discovered that the TcN moiety is extremely stable to hydrolysis and that the nitrido group remains firmly attached to the Tc atom throughout a number of substitution reactions.

According to the present invention, there is provided a novel group of compounds containing the TcN moiety, as well as methods for the preparation thereof and methods for the preparation of $^{99m}$Tc-radiopharmaceuticals utilizing these compounds.

According to a first aspect of the present invention, there are provided compounds of the formula I:

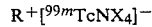

$$R^+[^{99m}TcNX_4]^- \qquad I$$

wherein $R^+$ is a cation, preferably a soluble cation such as sodium or another alkali metal, or ammonium, and X represents a halogen group, particularly a chloro or bromo group.

The compounds of this aspect of the invention are characterized by the presence of the nitridotetrahalotechnetium-99m anion in which Tc is in the $Tc^{VI}$ valency state, and which has been found to have particular utility in the preparation of radiopharmaceuticals containing the TcN moiety.

In another aspect of this invention, there is provided a process for the preparation of compounds of the formula I as described above, which comprises reaction of a compound containing the $^{99m}$Tc-pertechnetate anion ($R[^{99m}TcO_4]$, wherein R represents a cation such as alkali metal, or ammonium), with an azide compound, such as sodium azide, in the presence of a hydrohalic acid, such as hydrochloric or hydrobromic acid.

In another aspect, there is provided a method of producing a $^{99m}$Tc-labelled product, which comprises reacting a compound of the formula I with a ligand. Suitable ligands includes, for example, methylene diphosphonate (MDP), thiourea (TU), thiomalate (TMA), dimercaptosuccinate (DMSA), gluconate (GLUC), N-(2,6-diisopropylphenylcarbamoylmethyl)iminodiacetate (PIPIDA), N-(2,6-dimethylphenylcarbamoylmethyl)iminodiacetate (HIDA) ethane-1-hydroxy-1,1-diphosphonate (EHDP), diethylenetriaminepentaacetate (DTPA), and cysteine (CYS). Other ligands which may be used in accordance with the present invention include thiouracil, diethyldithiocarbamate, mercaptopyridine, mercaptopyrimidine, thiooxine, acetylacetone, pyridoxal, oxine, tropolone and tetracycline. Monoclonal antibodies which may also be labelled in accordance with the present invention, and which have been shown to retain their specificity following labelling. This aspect of the invention is described in greater detail hereinafter.

In yet another aspect, there is provided a $^{99m}$Tc-labelled product which comprises the reaction product of a compound of formula I with a ligand.

BRIEF DESCRIPTION OF THE DRAWINGS

FIGS. 1, 2, and 3 represent UV spectral studies.

Figure 3:
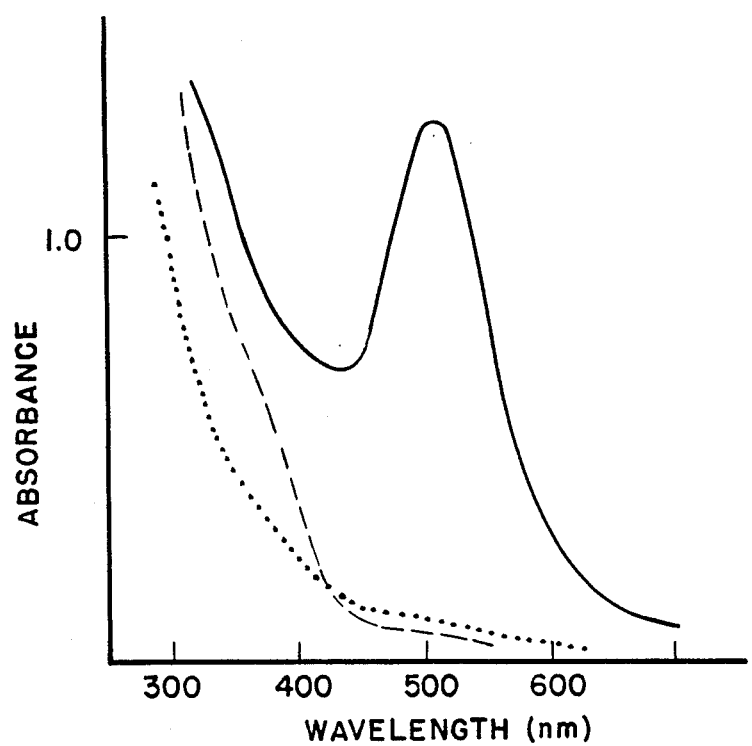

The desirability of using a substitution route for the preparation of $^{99m}$Tc-radiopharmaceuticals has long been recognized. However the method has suffered because of the difficulty in obtaining $^{99m}$Tc in a suitable chemical form at the Tc concentrations used for radiopharmaceutical production. The nitrido labelling technique described here is a comparatively simple method for the preparation of a wide range of radiopharmaceuticals based on the TcN moiety. While Tc is initially present as Tc(VI) in $TcNCl_4^-$, it has been found that reduction usually takes place to the Tc(V) state if the ligand has the ability to act as a reducing agent. Ligand substitution then takes place around the $TcN^{2+}$ core. In all cases studied to date, the presence of the nitrido group has been found to alter the biological behaviour of the $^{99m}$Tc-labelled ligand. Nitrido labelling has been found to be particularly suitable for the labelling of "soft" ligands.

The present invention has particular application in the coupling of $^{99m}$Tc to monoclonal antibodies (MAb) and the use of the resulting complexes, for example, in specific the detection of tumors in vivo, (see, for example, Rhodes, et al, 1982). At present a number of difficulties exist in the diagnostic radiolocalization of tumors, one of which is the choice of radionuclide. Many studies have used 131I, however this radionuclide has serious drawbacks including a poor quality image, significant radiation exposure due to its beta emissions, and short biological half-life.

Technetium —99m ($^{99m}$Tc) as an isotope for radiolocalization offers several advantages: it has a reasonably short half-life; it is cheap, easy to produce, and is readily available. The isotope has an optimal gamma energy (140 keV) for detection with currently available gamma scintigraphic instrumentation and produces very little radiation exposure to patients undergoing scanning procedures. However little use has been made of $^{99m}$Tc for labelling antibodies, presumably because most labelling methods used to date lead to loss of antibody activity, due to side reactions taking place and to transchelation reactions occurring in vivo.

In accordance with the present invention, compounds of the formula I described above have been found to produce stable $^{99m}$Tc-labelled MAb by a substitution reaction in the same manner as other ligands described herein. Either whole monoclonal antibodies, or antibody fragments (such as Fab fragments) which react with the corresponding antigens may be labelled in accordance with this invention. Antibody specificity is maintained in the labelling process and the labelled product is stable. In addition, tests have shown that when the labelled MAb is used in tumor detection, tumors may be visualized in as soon as two hours, and furthermore small tumors (about 0.4 cm) located near large vascular organs can be visualized.

Preferably, in labelling monoclonal antibody in accordance with this invention, the antibody is at least partially reduced for example by reaction with a reducing agent such as dithiothreitol, in order to convert disulfide linkages into sulfhydryl residues. Such a partial reduction procedure enables utilization of the presence of the TcN moiety for sulfur atoms, and thus enables the production of more stable complexes in which the MAb ligand is bound through sulfur atoms to the TcN moiety. It is also noted that these sulfhydryl groups would be removed from the sites responsible for antibody specificity, hence formation of the complexes is less likely to cause loss of specificity.

The following Examples illustrate the preparation of $[^{99m}TcNX_4]^-$ compound as well as the biological behaviour of TcN radiopharmaceuticals containing various ligands.

EXAMPLE 1

A. Preparation of sodium tetrachloronitridotechnetate Na$[^{99m}TcNCl_4]$ and $^{99m}$TcN-radipharmaceuticals.

Unless otherwise stated all solvents and chemicals were of analytical grade. L(+)-Cysteine for biochemistry was obtained from E. Merck, Darmstadt, Methylenediphosphonic acid (MDP) from Sigma Chemical Co., St. Louis and diethylenetriaminepentaacetic acid (DTPA) from Koch-Light Laboratories, Colnbrook. Sodium-2-gluconate was obtained from Fluka A. G. EHDP was prepared using the method described by Castronovo (1974).

HIDA and PIPIDA hydrochlorides were prepared by the reaction of the N-chloroacetanilides with iminodiacetic acid using a variation of the method of Callery et al (1976). A mixture of N-chloroacetanilide (0.05 mole), iminodiacetic acid (0.05 mole) and 10 g anhydrous sodium carbonate was refluxed in 30 mL of 75% aqueous ethanol for 6 hours. On cooling the solution was acidified with concentrated hydrochloric acid and the pH adjusted to 1.5. The precipitate was filtered and recrystallised from 50% aqueous ethanol. Use of sodium carbonate resulted in improved yields (>60%). $^{99}$Tc in the form of ammonium pertechnetate in 0.1M ammonium hydroxide solution was obtained from Amershal International.

(i) A solution of $^{99m}$Tc-pertechnetate (50 MCi~18 GBq for animal studies) were taken to dryness using a rotary evaporator. Sodium azide (~20 mg) was added to the dry residue, followed by 10 ml of concentrated hydrochloric acid (sg 1.18). The solution was refluxed for 5 minutes to complete the reduction and destroy excess azide before being taken to dryness in the rotary evaporator. 1 ml of ligand solution (PIPIDA 20 mg/ml, pH 7, all others 5 mg/ml, pH 7) was added followed by 2 ml saline. If necessary, the pH was adjusted to 6–7 by the additionof 0.1M sodium hydroxide. After filtration through a 0.22$\mu$ membrane filter, the radiopharmaceutical was ready for use.

(ii) An alternative labelling procedure is to perform the ligand replacement in a non-aqueous solvent, such as in acetonitrile or ethanol solution. By way of example, 10 ml of acetonitrile is added to the dry residue after the azide reduction followed by 100 $\mu$l of the ligand solution. After heating on a water bath for 10 minutes, the acetonitrile is removed in a rotary evaporator and the dried extract dissolved in 1 ml of the ligand solution and 2 ml saline as before.

B. Animal Distribution Studies 0.05–0.1 ml of the preparation (1–2 mCi) was injected into the tail vein of Swiss mice (20–30 g) and the activity injected measured in an ionization chamber. After injection, mice were allowed free access to food and water. At each time interval studied, three mice were sacrificed by cervical dislocation and dissected. Organs were weighed and their activities measured in the ionisation chamber. The original injected activity was corrected for the activity found in the tail. Blood activity was calculated on the assumption that the overall blood volume represents 7% of total body weight.

C. Measurement of $^{99m}$Tc Labelling

2 $\mu$L aliquots of each preparation were chromatographed on Whatman No. 1 paper in three solvent systems: saline, 70% methanol and methyl ethyl ketone. After development all papers were dried and scanned in a radiochromatogram scanner (Packard Model 7220/21). Where appropriate, peaks were cut from the strips and counted for $^{99m}$Tc activity in a gamma counter. All preparations contained less than 5% free pertechnetate.

D. UV Spectral Studies

Preparations were made using 300 $\mu$g $^{99}$Tc added as carrier for UV spectral studies. UV spectra were recorded on a Beckman Acta CII spectrophotometer.

Pertechnetate was reduced using the following reduction systems:

(i) concentrated hydrochloric acid,
(ii) concentrated hydrochloric acid/potassium iodide,
(iii) concentrated hydrochloric acid/sodium azide,
(iv) concentrated hydrochloric acid/stannous chloride,
(v) concentrated hydrochloric acid/hypophosphorous acid,
(vi) concentrated hydrochloric acid/hydroxylamine hydrochloride.

The spectra of all samples were measured in hydrochloric acid solution before and after heating on a hot plate.

UV spectra of the technetium complexes studied were obtained after taking the above solutions to dryness in a rotary evaporator and dissolving the dry residue in 1 ml ligand solution and 2 ml water. The pH of the solution was adjusted to 7 using either 0.1M or 1M sodium hydroxide.

E. RESULTS

The concentration of Tc in the solution used for uv absorption measurements was determined by beta counting. 10 mL scintillation fluid (Aquassure-NEN) were added to 0.1 mL aliquots of the solution for counting in a liquid scintillation spectrometer. Counting efficiency was determined by counting aliquots of a pertechnetate solution standardized by uv spectrophotometry. Quenching of the solution was checked by external standardization. An internal standard was added when a quench correction was necessary.

(i) UV Spectral Studies (a) Hydrochloric Acid Studies

Addition of potassium iodide, hydroxylamine hydrochloride, or hypophosphorous acid to pertechnetate in hydrochloric acid followed by heating all result in the formation of Tc(IV). This is shown in FIG. 1 by the characteristic UV absorption spectrum of $TcCl_6^{2-}$ which has an absorption maximumat 340 nm and a minor peak at 305 nm. Pertechnetate allowed to stand in concentrated hydrochloric acid in the cold, results in the production of $TcOCl_5^{2-}$ in which Tc is in the Tc(v) oxidation state. The UV spectrum however indicates that the $TcOCl_5^{2-}$ produced also contains Tc(IV), the proportion of which is increased by heating. Heating of pertechnetate in the presence of azide results in the formation of $TcNCl_4^-$ characterised by an absorption maximum at 395 nm ($=500$ m$^2$ mol$^{-1}$) and free of contaminating Tc(IV).

(b) MDP Complexes

The spectra of TcN-MDP and Tc(IV)-MDP are shown in FIG. 2. When MDP was added to $TcNCl_4^-$ at pH 5.5, a pink colored complex ($\lambda_{max}$—515 nm) was produced. On heating the pink color disappeared during a yellow complex with an adsorption maximum at 335 nm. The spectrum of this complex was identical to that obtained by adding MDP to $TcNCl_4^-$ and adjusting the pH to 10 ($\lambda_{max}=335$ nm, $\epsilon=21$ m$^2$ mol$^{-1}$).

(c) DTPA Complexes

When prepared at room temperature, TcN-DTPA showed an absorption maximum at 505 nm ($\epsilon=105$ m$^2$ mol$^{-1}$) (FIG. 3). On heating the peak disappeared producing a complex with no significant absorption in the range 300–800 nm. $Tc^{IV}$-DTPA produced by adding DTPA to $TcCl_6^{2-}$ showed no significant absorption maximum in the uv-vis region.

(d) Cysteine Complexes

The spectrum of TcN-CYS showed no significant absorption in the uv-visible region that could be attributed to the complex.

(ii) Stability of dried $TcNCl_4^-$ Preparation

Samples of the $^{99m}TcNCl_4^-$ preparation were taken to dryness in a rotary evaporator and stored for 24 hours (a) in air at room temperature, (b) at 80° C., and (c) at room temperature and 100% humidity. They were then used to prepare $^{99m}$TcN-DTPA by addition of ligand as before. No significant difference in chromatographic behaviour as measured by high performance liquid chromatography (HPLC) was observed in any sample indicating that the dry $^{99m}TcNCl_4^-$ reagent was stable for up to 24 hours.

(iii) Animal Distribution Studies (a) Results of biodistribution studies of $^{99m}$TcN-MDP, $^{99m}$TcN-DTPA and $^{99m}$TcN-CYS are given in Tables 1-3. $^{99m}$TcN-MDP was characterized by high blood pool activity and showed significant bone uptake. $^{99m}$TcN-DTPA showed similar renal excretion behaviour to $^{99m}$Tc-DTPA(Sn) and was probably excreted by a similar mechanism. Blood pool activity however was higher than that observed for $^{99m}$Tc-DTPA(Sn). $^{99m}$Tc-cysteine showed rapid clearance with high renal localization. Urinary excretion rates for the three $^{99m}$TcN-complexes are given in Table 4. Excretion rates of $^{99m}$TcN-MDP and $^{99m}$TcN-DTPA are significantly less than that of the respective $^{99m}$Tc(Sn)-complexes.

Figure 4:
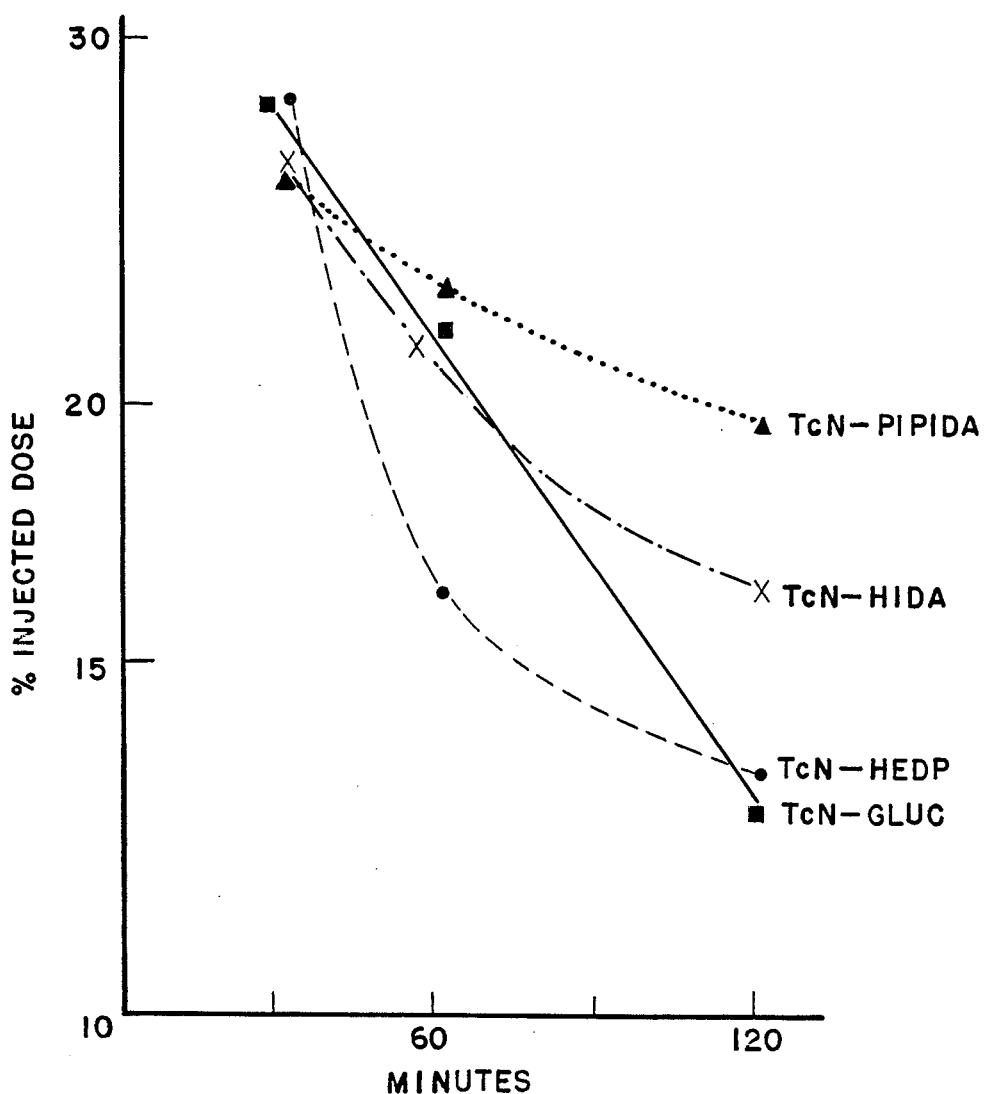
FIG. 4 represents animal distribution studies.

(b) Results of biodistrubition studies of $^{99m}$Tc-GLUC, $^{99m}$TcN-HEDP, $^{99m}$TcN-HIDA and $^{99m}$TcN-PIDIDA ae given in Tables 5-9. All preparations showed high blood pool activity with the $^{99m}$TcN-GLUC and $^{99m}$TcN-HEDP preparations clearing slightly faster than $^{99m}$TcN-PIPIDA and $^{99m}$TcN-HIDA. (FIG. 4). Overall, $^{99m}$TcN-GLUC, $^{99m}$TcN-HIDA and $^{99m}$TcN-HEDP showed comparable patterns of biological behaviour. $^{99m}$TcN-PIPIDA differed from the other agents in that it gave significantly higher activity in the intestines. With all preparations the clearance into the intestines took place essentially in the first 30 minutes. The higher clearance of $^{99m}$TcN-PIPIDA could be due to $^{99m}$TcN-PIPIDA undergoing a slower rate of exchange with serum proteins than $^{99m}$TcN-HIDA.

(c) Results of biodistribution studies of $^{99m}$TcN-DMSA are given in Table 10.

(iv) Stability studies

Stability studies of the dry $^{99}TcNCl_4^-$ preparations have indicated that the agent is sufficiently stable to be prepared in a central laboratory or manufacturing site and distributed to users for use in the preparation of $^{99m}$TcN-labelled radiopharmaceuticals. Preparation of the $^{99m}$TcN-radiopharmaceuticals in most cases takes place by simply dissolving the dry residue in a solution of the chelate.

$^{99m}TcNCl_4^-$ may also be used to label ligands that are insoluble inwater or which may be unstable in aqueous solutions. It is possible to extract the $^{99m}$TcN-activity from the dry salt residue into organic solvents such as acetonitrile. Labelling may be performed in the organic solvent which may then be removed by evaporation. Labelling with $^{99m}TcNCl_4^-$ takes place via a substitution mechaism and is expected to be less susceptible to the hydrolytic type reactions which occur with many other labelling procedures. In addition, the presence of the nitrido group modifies the chemistry of the Tc atom in that reactions with "soft" ligands are more favoured than when other reducing agents are used.

EXAMPLE 2

A. Preparation of $^{99m}$TcN-labelled MAb (i) Tumor Cell Lines

Two tumor cell lines were used: once, the E3 clonal variant of the thymoma ITT(1)75NS (Hogarth, et al, 1982), which was obtained by three successive rounds of cytofluorographic sorting of IGG(1)75NS cells stained with monoclonal Ly-2 antibodies and selected for the most fluorescent 1% of cells. The murine cell line E(3) was maintained in vitro in DME supplemented with 10% heat inactivated newborn calf serum (Flow Laboratories, Sydney, Australia), 2 mM glutamine (Commonwealth Serum Laboratories, CSL, Melbourne, Australia), 100 I.U./ml penicillin (CSL) and 100 mg/ml streptomycin (Glaxo, Melb., Aust.). E3 cells were washed twice in DMI (without additives) and twice in DME containing 0.5% BSA and used in the in vitro binding assays. The E3 cell line was maintained in vivo by the passaging of cells from ascites fluid produced in (B6×BALB/c)F$_1$ mice or from solid tumors which grow after the subcutaneous injection of $10^6$ or $10^7$ cells. The second cell line used was a human colonic carcinoma, COLO 205 (Semple et al, 1978). It was maintained in cuture with TPMI containing the same additives. Adherent COLO 205 cells were harvested with 0.125% trypsin (CSL) washed with RPMI and injected subcutaneously into nude mice, where tumors appeared after the injection of $2\times10^6 - 1\times10^7$ cells.

(ii) Monoclonal Antibodies (MAb)

Two monoclonal antibodies were used: (i) anti-Ly-2.1 (IgG2a), an antibody raised against the murine alloantigen Ly-2.1 (Hogarth et al, 1982) and (ii) 250-30.6 (IgG2b), an antibody to human colonic secretory epithelium (Thompson, et al, 1983). The monoclonal antibodies were isolated from ascitic fluid by precipitation with 40% saturated ammonium sulphate, followed by dissolution in 0.01M Tris buffer pH 8.0 and extensive dialysis against the same buffer. The crude antibody preparations were further purified by affinity chromatography using protein-A Sepharose (Pharmacia) and then purity determined by gel electrophoresis and antibody activity assayed by a rosetting test (Parish, et al, 1978).

(iii) $^{99m}$Tc Labelling of Antibodies $^{99m}$TcNCl$_4^-$ was prepared as described above. For labelling the MAb was first reduced with dithiothreitol (DTT) by adding 20 μl of DTT in PBS (115 mg/ml) to 200 μg of MAb (1 mg/ml in PBS) and standing the mixture at room temperature for 30 minutes after which the reduced MAb was separated from DTT by gel chromatography using 0.1M sodium acetate pH 4.0 as eluant on an 8 cm×1 cm column of Biogel P-6 (Biorad Laboratories, Richmond, USA). The fractions (1 ml) containing the protein peak were added to the dried $^{99m}$TcNCl$_4^-$ salt residue and the mixture brought to pH 3.0 with 0.2M hydrochloric acid. After 2 minutes at room temperature, 2 drops of 0.1M sodium phosphate was added and the pH adjusted to 7 by the careful addition of sodium hydroxide (1M or 0.1M). Purification of the labelled MAb was then achieved by gel chromatography with a Sephadex G-25 disposable column (PD-10, Pharmacia) equilibrated in PBS, 500 μl aliquots were collected and the radiolabelled protein peak identified by gamma counting.

B. RESULTS (i) In vitro stability and specificity of $^{99m}$TcN-MAb

Three different specificity assays were performed. The first compared the activity of $^{99m}$Tc labelled by Ly-2.1 MAb to thymocytes from the mouse strains RF/J (Ly-2.1 positive and C57BL/6 (Ly-2.1 negative). A ten fold difference was observed in the binding of the labelled MAb to the specific cells (RF/J) when compared to the negative cell controls (C57BL/6). The procedure used to couple $^{99m}$TcNCl$_4^-$ to MAb produced a stable complex which was shown to be stable and bind specifically antigen positive target cells ten times greater than antigen negative control cells.

In the second specificity assay two different MAb, one directed against colonic secretory epithelium (250-30.6) and the second the anti-Ly-2.1 MAb, were labelled with $^{99m}$Tc under identical coupling conditions and the two complexes were tested for their ability to bind to the murine T cell thymoma E3, which is positive for the Ly-2.1 antigen but does not react with the anti-colon antibody. The anti-Ly-2.1 MAb bound ten times more efficiently than the $^{99m}$TcN-anti-colon complex. The stability of the $^{99m}$TcN-MAb was demonstrated here, where only the antibody reactive complex ($^{99m}$TcN-anti-Ly-2.1) showed increased binding on E3 target cells. The non-reactive complex ($^{99m}$TcN-anti-colon) exhibited a significantly reduced uptake of radioactivity on the same target cells.

The stability of the TcN-MAb complexes was examined in a third assay. Aliquots of labelled MAb were stored at 4° C. overnight and the stability of the label was determined by binding the stored material to thymocytes. The labelled MAb were shown to be stable by their retention of binding ability. RF/J thymocytes (Ly-2.1+) bound better than 10 fold more labelled Ly-2.1 MAb than C57BL/6 thymocytes (Ly-2.1−). In three different specificity assays in the in vitro stability of the $^{99m}$TcN-MAb complexes was established and were shown to be chemically stable, even when allowed to stand at 4° C. overnight, binding only to antibody reactive target cells.

(ii) Localization

The in vivo localization and biodistribution of TcN-MAb complexes were preformed in separate studies. In the first, the mice were dissected normal organs, tumors and an aliquot of whole blood were counted in a gamma counter. The solid tissues were then weighed and the results were used to calculate the localization ratio derived as follows: tissue (cpm/g)/blood (cpm/g). Two groups of 16 (C57BL/6×BALB/c)F$_1$ mice bearing the E3 tumor (0.23-1.11 g) were injected i.v. via the tail vein, with one of two MAb (anti-Ly-2.1 or anti-colon carcinoma) labelled with $^{99m}$TcNCl$_4^-$ under identical conditions. (Each mouse received 115 μCi Tc and 10 μg MAb). In the data in Table 11, 4 mice from each group were sacrificed at different time intervals after injection (20, 30.5, 35 hrs) and the distribution of the specific MAb (anti-Ly-2.1) was calculated for the individual tissues and compared to the observed distribution of the non-reactive MAb (anti-colon). After 20 hrs the tumor localization was observed to be 3 times greater for the specific MAb than that observed for the non-specific MAb. This ratio increased to approximately 3.8 at 30.5 hrs, and 7.3 at 35 hrs after injection. It is important to point out that the E3 tumor was observed to have the highest localization ratio (i.e. tissue (cpm/g)/blood (cpm/g)) in the group injected with the specific MAb (anti-Ly-2.1) with the liver, spleen and kidney localization ratio being below or similar to the blood ratio. However, with the non-specific antibody (250-30.6) the liver, spleen and kidney were observed to be higher than the blood ratio, with the liver biodistribution ratio being 5 times greater than the blood after 30.5 hrs.

In the second study, a specific MAb (anti-Ly-2.1) was compared in two different tumors. Nude mice bearing colo 205 xenografts were used as the non-reactive tumor and the E3 as the positive tumor. The data was obtained 20 hrs after the injection of the anti-Ly-2.1 labelled MAb (Table 12). The E3 thymoma (Ly-2.1+) was observed to take up 3 times more radioactivity tha the colo 205 xenografts (Ly-2.1−H). The two biodistribution studies illustrate a significant increased incorporation of radioactivity in the MAb reactive tumor when compared to the levels of radioactivity in the blood and that incorporated in the other normal tissues.

TABLE 1

Biological Distribution of $^{99m}$TcN-MDP in mice*

| Time after Injection | % Injected Dose/Organ | | |
|---|---|---|---|
| | 30 min | 60 min | 120 min |
| Heart | 0.6(0) | 0.4(0) | 0.3(1) |
| Lung | 2.9(5) | 3.0(14) | 1.9(15) |
| Liver | 10.4(4) | 9.4(8) | 6.2(13) |
| Spleen | 0.4(1) | 0.3(1) | 0.4(1) |
| Stomach | 1.1(1) | 0.8(2) | 1.2(11) |
| Kidneys | 6.9(27) | 3.3(5) | 2.6(7) |
| Intestines | 4.3(4) | 4.1(6) | 6.1(13) |
| Femurs | 0.3(0) | 0.3(0) | 0.3(0) |
| Blood | 26.5(46) | 18.8(18) | 13.5(40) |
| | % Injected Dose/Gram Organ | | |
| Heart | 4.2(2) | 2.4(4) | 2.0(4) |
| Liver | 5.7(3) | 4.7(5) | 3.8(1) |
| Kidneys | 13.0(54)+ | 5.6(11) | 5.8(18) |
| Femurs | 1.7(2) | 1.4(2) | 1.5(1) |
| Blood | 13.0(22) | 8.1(3) | 6.7(19)+ |

Standard deviation of last significant digit(s) in brackets.
*n = 3 unless otherwise stated
+ 2 mice

TABLE 2

Biological Distribution of $^{99m}$TcN-DTPA in mice*.

| Time After Injection | % Injected Dose/Organ | | |
|---|---|---|---|
| | 30 min | 60 min | 120 min |
| Heart | 0.1(0) | 0.1(0) | 0.1(0) |
| Lung | 0.7(1) | 0.7(2) | 0.4(1) |
| Liver | 1.7(2) | 1.5(3) | 1.1(2) |
| Spleen | 0.1(0) | 0.1(0) | 0.1(0) |
| Stomach | 1.1(2) | 1.3(4) | 0.9(0) |
| Kidneys | 1.5(1) | 1.3(2) | 0.8(0) |
| Intestines | 2.1(4) | 2.0(3) | 2.1(2) |
| Femurs | 0.1(0) | 0.1(0) | 0.1(0) |
| Blood | 6.2(8) | 4.0(5) | 2.4(1) |
| | % Injected Dose/Gram Organ | | |
| Heart | 0.6(0) | 0.5(1) | 0.4(1) |
| Liver | 0.8(1) | 0.7(1) | 0.6(1) |
| Kidneys | 2.5(1) | 2.2(4) | 1.5(2) |
| Femurs | 0.5(1) | 0.4(1) | 0.4(1) |
| Blood | 2.8(5) | 1.8(2) | 1.2(0) |

Standard deviation of last significant digit(s) in brackets.
* n = 3

TABLE 3

Biological Distribution of $^{99m}$TcN-CYSTEINE in mice.*

| Time After Injection | % injected Dose/Organ | | |
|---|---|---|---|
| | 30 min | 60 min | 120 min |
| Heart | 0.1(0) | 0.1(0) | 0.1(0) |
| Lung | 0.8(2) | 0.5(1) | 0.4(1) |
| Liver | 2.7(5) | 1.6(1) | 1.3(1) |
| Spleen | 0.1(0) | 0.1(0) | 0.1(0) |
| Stomach | 0.4(1) | 0.3(3) | 0.3(1) |
| Kidneys | 4.4(5) | 3.4(5) | 2.8(2) |
| Intestines | 5.3(8) | 3.4(1) | 4.0(3) |
| Femurs | 0.2(0) | 0.1(1) | 0.1(0) |
| Blood | 4.9(7) | 2.8(4) | 1.8(1) |
| | % Injected Dose/Gram Organ | | |
| Heart | 0.7(1) | 0.5(2) | 0.4(2) |
| Liver | 1.3(2) | 0.8(2) | 0.6(1) |
| Kidneys | 7.4(11) | 6.2(9) | 4.8(5) |
| Femurs | 0.8(1) | 0.6(3) | 0.2(1) |
| Blood | 2.1(2) | 1.3(1) | 0.8(1) |

Standard deviation of last significant digit(s) in brackets.
* n - 3

TABLE 4

Urinary Clearance of $^{99m}$TcN-MDP, $^{99m}$TcN-DTPA and $^{99m}$TcN-CYS*

| | % Retained Activity | | |
|---|---|---|---|
| | $^{99m}$TcN-MDP | $^{99m}$TcN-DTPA | $^{99m}$TcN-CYS |
| 30 min | 71.9(43) | 24.8(42) | 35.8(43) |
| 60 min | 51.4(14) | 21.4(31) | 18.7(28) |
| 120 min | 44.7(57) | 14.6(6) | 15.7(15) |

Standard deviation of last significant digit(s) in brackets.
* n = 3

TABLE 5

Biological Distribution of $^{99m}$TcN-GLUC in mice.

| Time After Injection | % Injected Dose/Organ | | |
|---|---|---|---|
| | 30 min | 60 min | 120 min |
| Heart | 0.7(0.1) | 0.7(0.1) | 0.4(0.1) |
| Lung | 2.2(0.6) | 3.0(0.5) | 1.4(0.2) |
| Liver | 6.4(1.6) | 6.2(1.7) | 7.1(2.1) |
| Spleen | 0.3(0.1) | 0.3(0.1) | 0.2(0.1) |
| Stomach | 1.4(0.4) | 1.5(0.4) | 1.6(0.7) |
| Kidneys | 4.7(0.6) | 3.9(0.3) | 3.4(0.1) |
| Intestines | 5.4(0.7) | 4.1(0.8) | 7.0(1.4) |
| Femurs | 0.3(0.0) | 0.3(0.0) | 0.2(0.1) |
| Blood | 25.7(2.3) | 21.7(3.6) | 12.7(1.9) |
| | % Injected Dose/Gram Organ | | |
| Heart | 4.5(0.7) | 4.6(1.0) | 2.6(0.6) |
| Liver | 3.3(0.8) | 3.1(0.9) | 3.3(0.8) |
| Kidneys | 8.4(1.0) | 6.6(0.7) | 5.6(0.6) |
| Femurs | 1.7(0.1) | 1.3(0.1) | 0.8(0.2) |
| Blood | 12.0(1.0) | 9.5(1.8) | 5.2(0.3) |

Standard deviation in brackets.
n = 3.

TABLE 6

Biological Distribution of $^{99m}$TcN-HEDP in mice.

| Time After Injection | % Injected Dose/Organ | | |
|---|---|---|---|
| | 30 min | 60 min | 120 min |
| Heart | 0.5(0.0) | 0.3(0.0) | 0.3(0.0) |
| Lung | 2.5(0.6) | 1.8(0.3) | 1.5(0.4) |
| Liver | 12.1(0.3) | 9.0(1.0) | 7.7(0.5) |
| Spleen | 0.6(0.1) | 0.3(0.0) | 0.3(0.1) |
| Stomach | 0.6(0.1) | 0.7(0.1) | 0.6(0.1) |
| Kidneys | 4.1(0.2) | 3.2(0.2) | 3.0(0.2) |
| Intestines | 6.9(0.5) | 7.0(0.2) | 6.8(0.6) |
| Femurs | 0.5(0.0) | 0.5(0.1) | 0.4(0.1) |
| Blood | 28.0(5.0)≠ | 16.2(2.0) | 13.2(1.0)≠ |
| Heart | 4.3(0.5) | 2.4(0.3) | 2.3(0.2) |
| Liver | 8.1(0.8) | 5.5(0.7) | 4.8(0.4) |
| Kidneys | 9.1(0.4) | 6.5(0.4) | 6.1(0.3) |
| Femurs | 3.4(0.5) | 3.1(0.8) | 2.7(0.6) |
| Blood | 16.2(1.0)≠ | 7.3(1.1) | 7.7(0.5)≠ |

Standard deviation in brackets.
n = 3 unless otherwise stated.

TABLE 7

Biological Distribution of $^{99m}$TcN-HIDA in mice.

| Time After Injection | % Injected Dose/Organ | | |
|---|---|---|---|
| | 30 min | 60 min | 120 min |
| Heart | 0.4(0.1) | 0.4(0.0) | 0.2(0.0) |
| Lung | 2.3(0.3) | 2.0(0.3) | 1.2(0.3) |
| Liver | 7.2(1.4) | 6.7(1.2) | 3.6(0.2) |
| Spleen | 0.4(0.1) | 0.3(0.0) | 0.1(0.0) |
| Stomach | 1.1(0.2) | 2.0(0.4) | 1.0(0.0) |
| Kidneys | 3.5(0.2) | 3.4(0.2) | 2.1(0.0) |
| Intestines | 6.8(1.0) | 9.2(0.4) | 6.9(0.2) |
| Femurs | 0.3(0.1) | 0.4(0.0) | 0.2(0.0) |
| Blood | 25.8(1.6) | 20.6(1.3) | 16.3(2.2) |
| | % Injected Dose/Gram Organ | | |
| Heart | 2.9(0.5) | 2.7(0.4) | 1.6(0.1) |
| Liver | 4.2(0.8) | 3.9(0.6) | 2.1(0.1) |
| Kidneys | 6.9(0.5) | 6.7(0.4) | 4.2(0.1) |

TABLE 7-continued

Biological Distribution of $^{99m}$TcN-HIDA in mice.
% Injected Dose/Organ

| Time After Injection | 30 min | 60 min | 120 min |
|---|---|---|---|
| Femurs | 2.0(0.4) | 2.3(0.1) | 1 0(0.1) |
| Blood | 13.6(0.6) | 10.8(0.6) | 8.7(1.1) |

Standard deviation in brackets.
n = 3.

TABLE 8

Biological Distribution of $^{99m}$TcN-PIPIDA in mice.
% Injected Dose/Organ

| Time After Injection | 30 min | 60 min≠ | 120 min |
|---|---|---|---|
| Heart | 0.4(0.0) | 0.3(0.1) | 0.4(0.1) |
| Lung | 2.3(0.3) | 1.8(0.6) | 1.8(0.2) |
| Liver | 14.6(1.0) | 16.2(6.1) | 10.1(1.0) |
| Spleen | 0.2(0.1) | 0.3(0.0) | 0.2(0.0) |
| Stomach | 0.7(0.1) | 1.0(0.0) | 0.8(0.1) |
| Kidneys | 4.6(0.5) | 7.6(5.6) | 3.3(0.1) |
| Intestines | 12.8(1.5) | 12.0(0.8) | 14.9(2.1) |
| Femurs | 0.3(0.0) | 0.2(0.0) | 0.2(0.0) |
| Blood | 26.8(3.0) | 23.2(0.4) | 20.0(3.7) |
| % Injected Dose/Gram Organ | | | |
| Heart | 3.4(0.2) | 2.1(0.8) | 2.8(0.5) |
| Liver | 8.8(0.6) | 8.9(3.1) | 5.8(0.8) |
| Kidneys | 9.4(0.6) | 14.1(7.2) | 6.3(0.2) |
| Femurs | 2.0(0.3) | 1.1(0.1) | 1.0(0.2) |
| Blood | 14.8(1.9) | 11.5(0.7) | 10.2(1.5) |

Standard deviation in brackets.
≠n = 3.

TABLE 9

Urinary Clearance of $^{99m}$TcN-GLUC, $^{99m}$TcN-HEDP, $^{99m}$TcN-HIDA and $^{99m}$TcN-PIPIDA

| | % Retained Activity | | | |
|---|---|---|---|---|
| | $^{99m}$TcN-GLUC | $^{99m}$TcN-HEDP | $^{99m}$TcN-HIDA | $^{99m}$TcN-PIPIDA |
| 30 min | 72.6(4.2) | 68.8(9.5) | 74.9(5.8) | 79.5(1.2) |
| 60 min | 59.3(6.4) | 52.2(1.2) | 66.3(0.9) | 73.2(2.7) |
| 120 min | 45.6(5.6) | 47.2(4.5) | 54.7(1.1) | 62.0(2.5) |

Standard deviation in brackets.
n = 3.

TABLE 10

Biological distribution of $^{99m}$TcN-DMSA
% Injected Dose/Organ

| Time after Injection | 30 min | 60 min | 120 min |
|---|---|---|---|
| Heart | 0.3(0.0) | 0.3(0.0) | 0.2(0.0) |
| Lung | 1.6(0.1) | 1.1(0.2) | 1.1(0.2) |
| Liver | 4.3(0.1) | 3.9(0.3) | 3.4(0.2) |
| Spleen | 0.4(0.1) | 0.4(0.1) | 0.3(0.0) |
| Stomach | 0.6(0.1) | 0.7(0.2) | 0.5(0.1) |
| Kidney | 10.3(0.5) | 12.3(0.8) | 17.1(0.7) |
| Intestines | 5.3(0.7) | 5.1(0.4) | 4.8(0.5) |
| Femurs | 0.5(0.1) | 0.5(0.0) | 0.4(0.1) |
| Blood | 18.0(1.7) | 13.5(0.9) | 9.5(0.5) |
| Urine | 39.9(11.4) | 57.8(4.4) | 65.3(4.3) |
| % Injected Dose/Gram Organ | | | |
| Heart | 1.8(0.1) | 1.8(0.2) | 1.2(0.0) |
| Liver | 2.0(0.2) | 2.1(0.3) | 1.7(0.2) |
| Kidney | 16.4(0.7) | 22.2(1.4) | 29.0(2.9) |
| Femurs | 2.0(0.5) | 2.4(0.2) | 1.9(0.4) |
| Blood | 7.1(0.8) | 6.4(0.3) | 4.1(0.2) |

Standard Deviation in brackets
n = 3.

TABLE 11

Biodistribution Ratio Tissue (cpm/g): Blood (cpm/g)
Specific MAb (anti-Ly-2.1)/Non-specific Mab (anti-colon)

| | Time after Injection | | | | | |
|---|---|---|---|---|---|---|
| Organ | 20 hrs | | 30.5 hrs | | 35 hrs | |
| | α2.1 | 30.6 | α2.1 | 30.6 | α2.1 | 30.6 |
| Blood | 1.00 | 1.00 | 1.00 | 1.00 | 1.00 | 1.00 |
| Tumor (0.23–1.11 g) | 1.23 | 0.40 | 2.60 | 0.68 | 3.48 | 0.48 |
| Stomach | 0.08 | 0.12 | 0.12 | 0.17 | 0.07 | 0.12 |
| Spleen | 0.59 | 1.12 | 0.56 | 1.83 | 0.71 | 2.09 |
| Kidney | 0.77 | 1.48 | 0.94 | 2.14 | 0.92 | 2.50 |
| Heart | 0.33 | 0.39 | 0.19 | 0.17 | 0.33 | 0.19 |
| Liver | 0.84 | 0.27 | 1.02 | 3.26 | 1.20 | 5.19 |
| Lung | 0.38 | 0.22 | 0.86 | 0.66 | 0.36 | 0.60 |
| Intestine | 0.09 | 0.16 | 0.15 | 0.20 | 0.09 | 0.19 |
| Tail | 1.45 | 0.90 | 0.78 | 1.92 | 1.14 | 1.66 |

TABLE 12

Biodistribution Ratio Tissue (cpm/g): Blood (cpm/g)

| | ITT(1)E3 | COLO 205 | E3/COLO 205 |
|---|---|---|---|
| Blood | 1.0 | 1.0 | 1.0 |
| Tumor | 1.23 | 0.30 | 4.10 |
| | (.39–1.11 g) | (0.5–1.5 g) | |
| Stomach | 0.08 | 0.2 | 0.04 |
| Spleen | 0.59 | 0.60 | 0.98 |
| Kidney | 0.77 | 0.76 | 1.01 |
| Heart | 0.33 | 0.39 | 0.85 |
| Liver | 0.84 | 0.56 | 1.50 |
| Lung | 0.38 | 0.42 | 0.90 |
| Intestine | 0.09 | 0.15 | 0.60 |

REFERENCES

1. Castronovo, F. P., *J. Nucl. Med.* 15, 127 (1974).
2. Callery, P. S., Faith, W. C., Loberg, M. D., Fields, A. T., Harvey, E. B. and Cooper, M. D. *J. Med. Chem,* 19, 962 (1976).
3. Deutsch, E., Libson, K., Jurisson, S. et al: Technetium chemistry and technetium radiopharmaceuticals. *Prog. Inorg. Chem* 30: 75–139, 183.
4. Deutsch, E., Barnett, B. L.: Synthetic and structural aspects of technetium chemistry as related to nuclear medicine, in: Inorganic Chemistry in Biology and Medicine (ed Martel A. E.), ACS Symp. Series No. 150, Washington, *Amer. Chem. Soc.* 1980, pp. 103–119.
5. Hogarth, P. M., Henning, M. M. and McKenzie, I. F. C. The alloantigenic phenotype of radiation induced thymomas in the mouse. *J. N. C. I.* 1982; 69: 619–626.
6. Hogarth, P. M., Edwards, J., McKenzie, I. F. C., Goding, J. W. and Liew, F. Y. Monoclonal antibodies to murine Ly-2.1 surface antigen, *Immunology* 1982; 46: 135–144.
7. Parish, C. R. and McKenzie, I. F. C. A sensitive rosetting method for detecting subpopulations of Lymphocytes which react with alloantisera. *J. Immunol. Methods* 1978; 20: 173–183.

8. Rhodes, B. A. and Burchiel, S. W. Radiolabelling of Antibodies with Technetium 099m. Radioimmunoimaging and Radioimmunotherapy. Editors Burchiel, S. W. and Rhodes, B. A. Elsevier publishing Co. 1983, p. 207.

9. Semple, T. U., Quinn, L. A., Woods, L. F. and Moore, G. E. Tumor and Lymphoid cell lines from a patient with carcinoma of the colon for a cytoxicity model. *Cancer Res.* 1978; 38: 1345-1355.

10. Thompson, C. H., Jones, S. L., Pihl, E. and McKenzie, I. F. C. Monoclonal antibodies to human colon and colorectal carcinoma. *Br. J. Cancer* 1983; 47: 595-605.

11. Tubis, M., Krishnamurthy, G. T., Endow, J. S., Blahd, W. H. (1975)-$^{99m}$Tc-Penicillamine complexes-:In:Subramanian G., Rhodes, B. A., Cooper, J. F., Sodd, V. J. (eds) "Radiopharmaceuticals". The Society of Nuclear Medicine Inc., New York, pp. 55-62.

We claim:

1. A compound of the formula I:

$$R^+[^{99m}TcNX_4]^-  \quad I$$

wherein R+ represents a catio and X represents a halogen group.

2. A compound according to claim 1, wherein R+ represents a sodium or another alkali metal or ammonium cation, and X represents a chlorine or bromine atom.

3. A process for preparing a compound of the formula I defined in claim 1, which comprises reaction of a compound of the formula II:

$$R^+[^{99m}TcO_4]^- \quad II$$

wherein R+ is as defined in claim 1, with an azide compound in the presence of a hydrohalic acid.

4. A process according to claim 3, wherein R+ represents a sodium or another alkali metal or ammonium cation, the azide compound is sodium azide, and the hydrohalic acid is hydrochloric or hydrobromic acid.

* * * * *